United States Patent [19]

Szirth

[11] Patent Number: 5,262,806
[45] Date of Patent: Nov. 16, 1993

[54] PHOTO-DEVIOMETER

[75] Inventor: Bernard C. Szirth, Los Angeles, Calif.

[73] Assignee: Research Development Foundation, Carson City, Nev.

[21] Appl. No.: 832,825

[22] Filed: Feb. 7, 1992

Related U.S. Application Data

[63] Continuation-in-part of Ser. No. 226,174, Jul. 29, 1988, abandoned, which is a continuation-in-part of Ser. No. 600,339, Oct. 19, 1990, abandoned.

[51] Int. Cl.$^5$ ............................................. A61B 3/14
[52] U.S. Cl. ................................... 351/210; 351/206; 351/209; 351/222
[58] Field of Search ............... 351/203, 204, 205, 208, 351/209, 210, 206, 222, 223, 224

[56] References Cited

U.S. PATENT DOCUMENTS 4,279,478  7/1981  Matsumura ..................... 351/224
4,312,574  1/1982  Wilms .............................. 351/206

OTHER PUBLICATIONS

B. C. Szirth, et al., The Photo-Deviometer, Journal of Ophthalmic Photography, Sep. 1986, pp. 55-59.

*Primary Examiner*—Bruce Y. Arnold
*Assistant Examiner*—Hung Xuan Dang
*Attorney, Agent, or Firm*—Fulbright & Jaworski

[57] ABSTRACT

Disclosed is a photo-deviometer by which accurate and reproducible measurements and photographs are obtained on a wide range of patients of all ages and ethnic background affected by strabismus.

2 Claims, 8 Drawing Sheets

PHOTO-DEVIOMETER

CROSS REFERENCE TO RELATED APPLICATIONS

This application is a continuation-in-part to U.S. application Ser. No. 226,174 filed July 29, 1988, now abandoned, and a continuation-in-part to U.S. application Ser. No. 600,339 filed Oct. 19, 1990 now aband.

FIELD OF THE INVENTION

The present invention is in the field of strabismus for deviometry and photography.

BACKGROUND OF THE INVENTION

Strabismus is an extraocular muscle disorder resulting in misalignment of the eyes. It is reported to affect one to three percent of the population in the United States (Helveston E. M., "The Incidence of Amblyopia ex Anopsia in Young Adult Males in Minnesota in 1963" *Am. J. Ophthal.*, 60:75-77, 1965; Florm McNeomaier, RW, "Prevalence of Amblyopia" *Public Health Rep.* 8:29:34, 1966). Ophthalmic photographers are often asked to document this ocular misalignment both before and after strabismus surgery. The resulting photographs are then used for comparative studies, case presentations, teaching tools, and publications. It is thus important to generate accurate and reproducible photographs on a wide range of patients of all ages and ethnic backgrounds affected with strabismus. The present invention is directed to a gaze fixation device for strabismus photography (nine gaze cardinal photography) and deviometry which is referred to herein as the photodeviometer.

Deviometry, the measurement of strabismus in the cardinal positions of gaze, was initially developed as a method of documenting incomitance of strabismus, particularly in the case of a paretic vertically acting muscle.

The first deviometer, the Owen's deviometer (3), was designed in 1947 and consisted of a rotating arm (15.4 cm long) with a near fixation light set at 35.5 cm away from the patient. The angle of fixation remained at 25° from the primary position throughout the different positions of gaze. The deviation was then determined objectively by using the prism and cover test. The major disadvantage of the Owen's deviometer was the lack of an accommodative fixation target. Since adequate control of accommodation was not possible, inaccurate and variable measurements resulted.

Methods other than deviometry for documenting gaze incomitance have been described. The most common clinical method is to passively turn the patient's head so that the eyes are in the intended positions of gaze. The problem with this technique is the difficulty in obtaining consistency of head position. A slight head tilt, chin elevation or depression can easily be introduced. This method is rarely satisfactory because of inaccuracy and inconsistent measurements.

An ideal deviometer would allow measurements in the cardinal positions of gaze while the patient's head remains stationary. Also, it would be highly advantageous to have a central fixation target or images and accommodative fixation target or images set for deviometry or measurements and fixation targets or images set for extraocular muscle dysfunction, such as 25° and 34°, and the position of the recording devices, for example, a 35 mm single lens reflex (SLR) camera or a video camera. Such a photo-deviometer fulfills and meets all of these requirements and allows accurate and reproducible pre and post treatment measurements and/or photographs.

Prior Art

A preliminary search was made in the U.S. Patent Office for the subject matter hereof and the following patents are considered to be the most pertinent developed in this search.

U.S. Pat. No. 2,132,520 discloses a device for photographing the human eye which includes a card 72 which is read by the subject. The card 72 is located beyond the camera lens 42.

U.S. Pat. No. 2,229,721 discloses a camera and apparatus for photographing the human eye which includes a vertical board 18 providing for mounting matter to be viewed by the subject. The board 18 is mounted above the camera casing 10. A "bite bar" 20 is used to immobilize the subject.

U.S. Pat. No. 2,257,331 discloses a fundus camera which has no associated target means for directing eye movement.

U.S. Pat. No. 2,288,216 as related to the subject matter of this application is essentially the same as that of U.S. Pat. No. 2,132,520.

U.S. Pat. No. 2,288,430 discloses an apparatus for scanning and recording eye movement. Photo-electric cells are used for receiving a reflected image from light projected on to a subject's cornea. The subject views material on a wall mounted on top of the apparatus.

U.S. Pat. No. 3,944,342 discloses a slit lamp and a camera for a binocular microscope.

U.S. Pat. No. 4,504,129 discloses a camera-slit-lamp combination for routine eye examinations.

The following patents were developed in the search but are considered to be of secondary importance: U.S. Pat. Nos. 2,724,305; 3,467,466; 3,583,794; 3,724,932; 3,827,789; and 4,146,311.

None of the prior art developed in the search recognizes or solves the problems set forth above; for example (1) "lack of accommodative value" in the prior art deviometers; (2) the failure to produce different and easily identifiable images at each fixation target; and (3) the realization that over action and under action of oblique muscles are not always apparent at 25° fixation. The prior art devices do not provide (4) both inner row and outer row fixation pictures for deviometry and extraocular muscle dysfunction measurements; (5) structure to accommodate patients with ptotic eyelids; (6) a central fixation device in the camera; modified camera optics; modified controls/activator for the camera mirror; and patient's centering means by which accurate and reproducible pre and post treatment measurements and/or photographs can be obtained.

SUMMARY OF THE INVENTION

The present invention is directed to such a photo-deviometer which overcomes the problems of the prior art devices and provides a device which provides accurate and reproducible photographs on a wide range of patients of all ages and ethnic backgrounds affected with strabismus.

Advantageously, the present invention allows measurements in the cardinal position of gaze while the patient's head remains stationary, provides an accommodative fixation target, the angle of which in the position of the recording device relative to the patient are standardized by which accurate and reproducible pre and post treatment measurements and/or photographs are obtained.

The photo-deviometer includes a support structure, a deviometer disk mounted on the structure provided with a central fixation opening, and includes an inner row and an outer row of fixation images for deviometry and extraocular muscle dysfunction measurements. An electric selector and illuminating means are provided for selectively illuminating the fixation images. A recording device, such as a 35 mm camera, is mounted on the support structure and its lens is aligned with the center of the deviometer disk. An adjustable headrest for fixing a patient's head is mounted on the support structure on the other side of the deviometer disk. The recording device, central fixation opening, and the patient's eyes, when the headrest is in adjusted position, provide central fixation with respect to the recording plane.

Preferably, there are eight inner and eight outer fixation images. The inner and outer fixation images are disposed at 12:00, 1:30, 3:00, 4:30, 6:00, 7:30, 9:00, and 10:30 o'clock positions.

The inner row of fixation images is set for deviometry measurements, and the outer row of fixation images is set at a greater angle for the recording on film of the extraocular muscle dysfunction.

Preferably, the recording device is a 35 mm camera provided with a ring flash mounted directly on its lens.

Accordingly, it is an object of the present invention to provide a photo-deviometer by which accurate and reproducible pre and post treatment measurements and/or photographs can be obtained.

A further object of the present invention is the provision of a photo-deviometer provided with a central accommodative fixation target.

A further object of the present invention is the provision of a photo-deviometer which provides different and easily identifiable images at a plurality of fixation targets.

It is a further object of the present invention to provide a photo-deviometer which accommodates over action and under action of oblique muscles not always apparent at normal deviometry angles, for example, 25°.

It is a further object of the present invention to provide a photo-deviometer provided with both an inner row and an outer row fixation images for extraocular muscle dysfunction measurements and the photographic documentation of the extraocular muscle dysfunction.

A still further object of the present invention is the provision of a photo-deviometer which accommodates patients with ptotic eyelids.

It is a further object of the present invention to provide a photo-deviometer including a support structure, a deviometer disk mounted on the structure and provided with a central fixation opening, and an inner row and an outer row fixation images for deviometry and extraocular dysfunction measurements, electronic selectric illuminating means effective to selectively illuminate the fixation images, a recording device mounted on the support structure on one side of the deviometer disk, and an adjustable headrest for fixing a patient's head on the other side of the deviometer disk so that the patient's eyes, when the head rest is in an adjusted position, is in central fixation with respect to the plane of the recording device through the central of the opening in the deviometry disk.

It is a further object of the present invention to provide such a photo-deviometer device in which there are eight inner and eight outer fixation images, the inner and outer fixation images being located at 12:00, 1:30, 3:00, 4:30, 6:00, 7:30, 9:00, and 10:30 o'clock positions.

It is a further object of the present invention to provide such a photo-deviometer in which the inner row of fixation images is set for deviometry measurements and the outer row of fixation images is set at a greater angle for extraocular muscle dysfunction in an up and down gaze of the patient.

A still further object of the present invention is the provision of such a photo-deviometer in which the inner row of fixation images is set at 25°, and the outer row of fixation images is set at 34°.

It is a further object of the present invention to provide such a photo-deviometer in which the recording device is a 35 mm camera provided with a ring flash mounted directly on its lens.

Another object of the present invention is the provision of external fixation devices for measuring exaggerated or maximum eye movement.

Still a further object is the provision of a video monitor and screen for viewing a patient's eyes when the patient is in position in the photo-deviometer.

Other and further objects, features, and advantages appear throughout and are inherent in the photo-deviometer.

DESCRIPTION OF PREFERRED EMBODIMENTS

Figure 1:
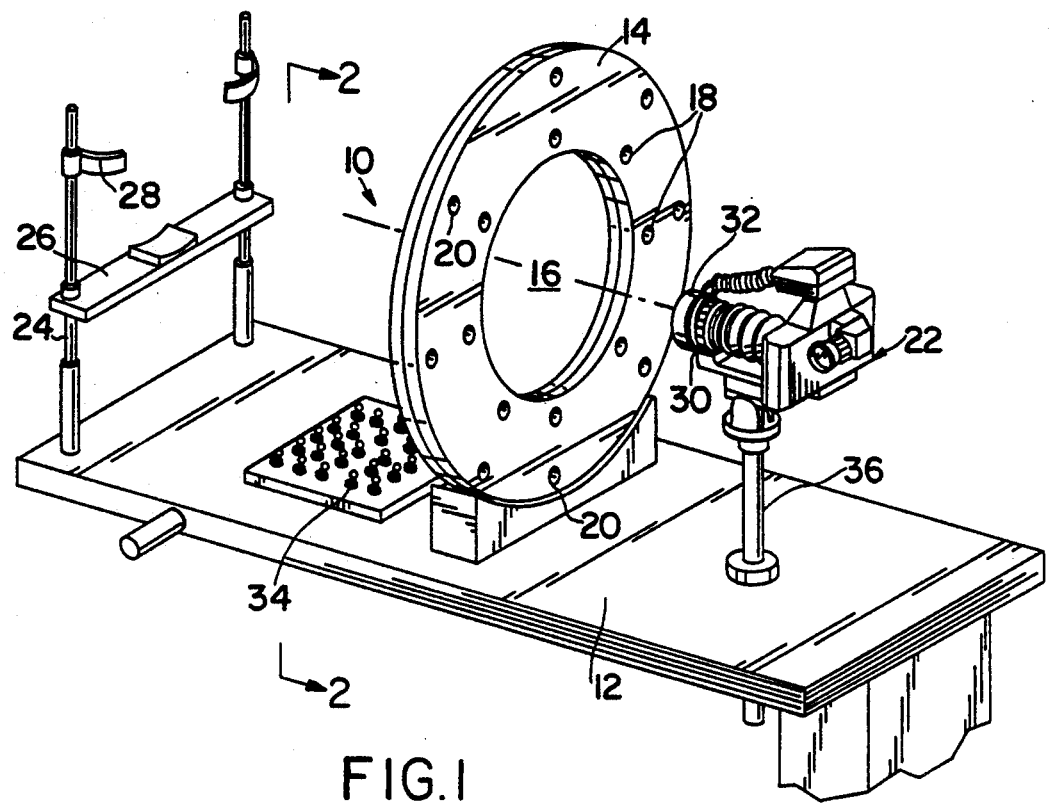
FIG. 1 is a perspective view of a photo-deviometer according to the present invention.

Referring now to the drawings and particularly to FIG. 1, the photo-deviometer is generally indicated by the reference numeral 10 and includes a support structure 12, here shown as an adjustable table. A deviometer disk 14 is mounted on the table 12 and is provided with a central fixation opening 16 and fixation images target 18 for deviometry measurements and fixation target or images 20 for extraocular dysfunction measurement, here shown as an inner row 18 and an outer row 20 of fixation images 17. Mounted adjacent one end of the table 12 is a recording device 22, here shown as a 35 mm camera, and mounted on the other side of the deviometer disk 14 is an adjustable headrest 24. The headrest 24 includes an adjustable chin rest 26 and an adjustable forehead headrest 28 for fixing the patient's head, not shown, so that the patient's eyes are in a central fixation position with respect to the central fixation opening 16 and the lens 30 of the recording device 22 which is provided with the ring flash 32 mounted directly on the lens 30.

The inner and outer row of fixation images 18 and 20 are positioned at 12 o'clock, 1:30, 3:00, 4:30, 6:00, 7:30, 9:00 and 10:30 positions.

As illustrated, recording device 22 is adjustable mounted on the table 12 for aligning the lens 30 of the camera in a central fixation position with respect to the central fixation opening 16 and the plane of the film in the camera.

The deviometer or image wall 14 is provided with images, not shown, positioned so that a patient can see the images when they are illuminated. Preferably, the images 17 selected are from Walt Disney characters as the cartoon figures are easily identifiable by most children regardless of ethnic background and language barriers, they are not violent, and these characters will probably endure over future generations.

Also disposed on the table 12 are the selector switches 34 for selectively illuminating the visual images on the inner and outer rows 18 and 20 of the deviometer disk 14.

Figure 4:
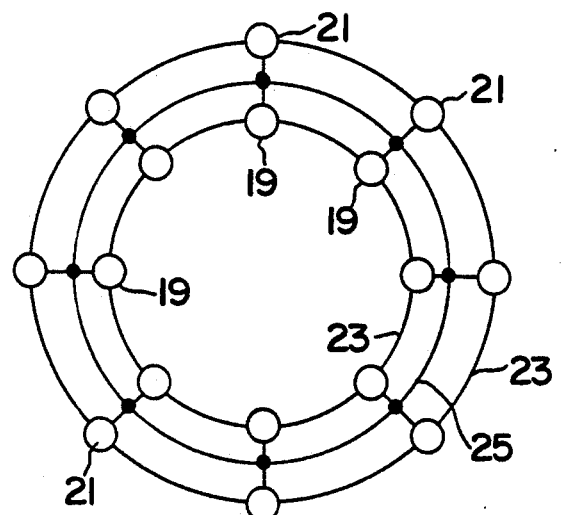
FIGS. 4 and 5 are diagrams of the electrical system of the photo-deviometer of FIGS. 1, 2, and 3.
Figure 5:
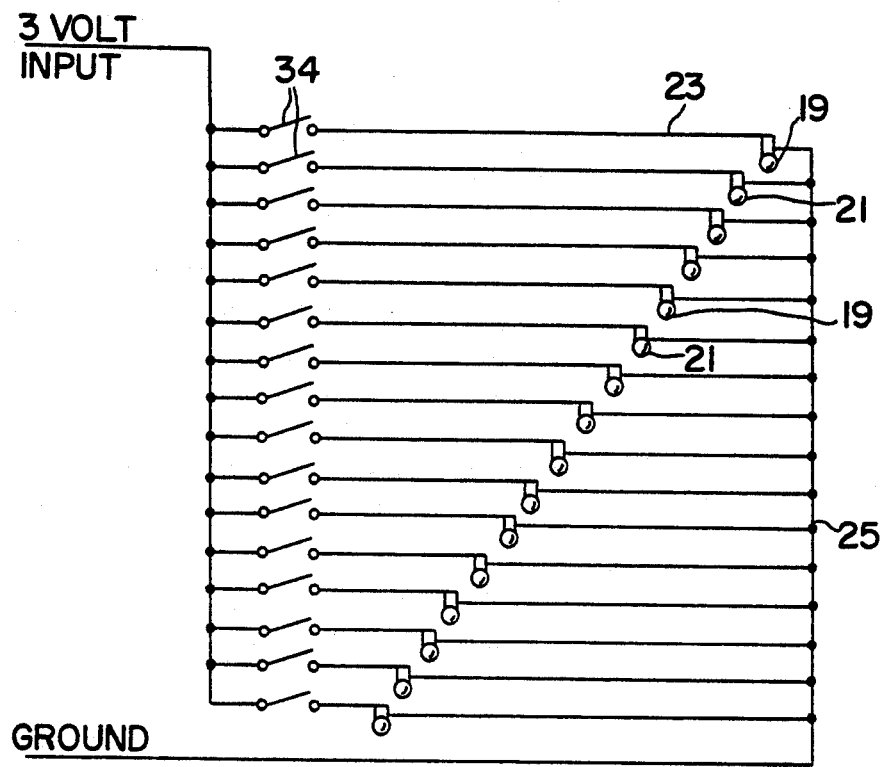
Figure 6:
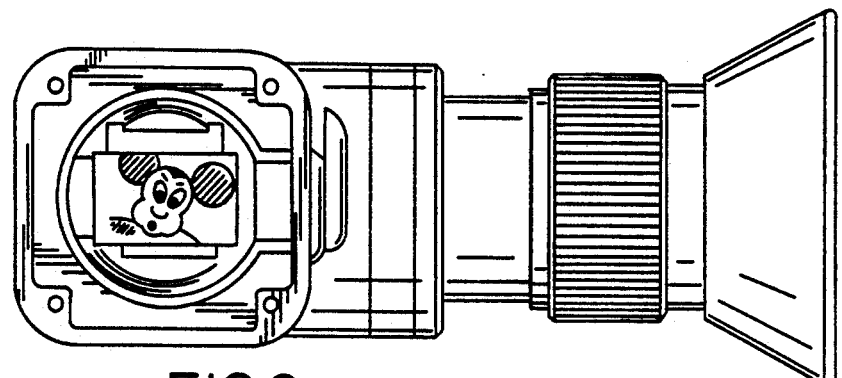
FIG. 6 is a view of the camera fixation device and modified optics.

Referring now to FIGS. 4 and 5, an electrical diagram illustrated for illuminating the inner 18 and outer 20 images by the electric bulbs 19 and 21, respectively. Positive lines 25 are connected to each of the switches 34 and to each of the bulbs 19 and 21, which in turn are connected to the ground 23. Thus, activation of a switch 34 illuminates an image. No more description of the electrical systems for illuminating the images 17 is given or deemed necessary as any desired electrical system for this purpose can be used.

Figure 3:
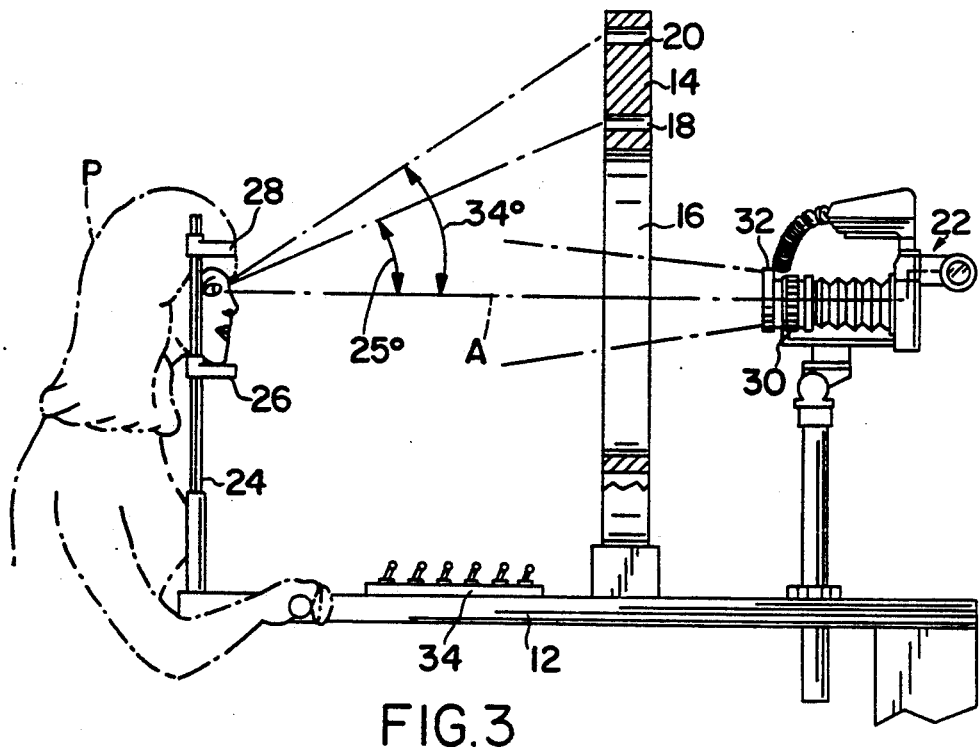
FIG. 3 is a side view of the photo-deviometer of FIGS. 1 and 2 with a patient in position.
Figure 2:
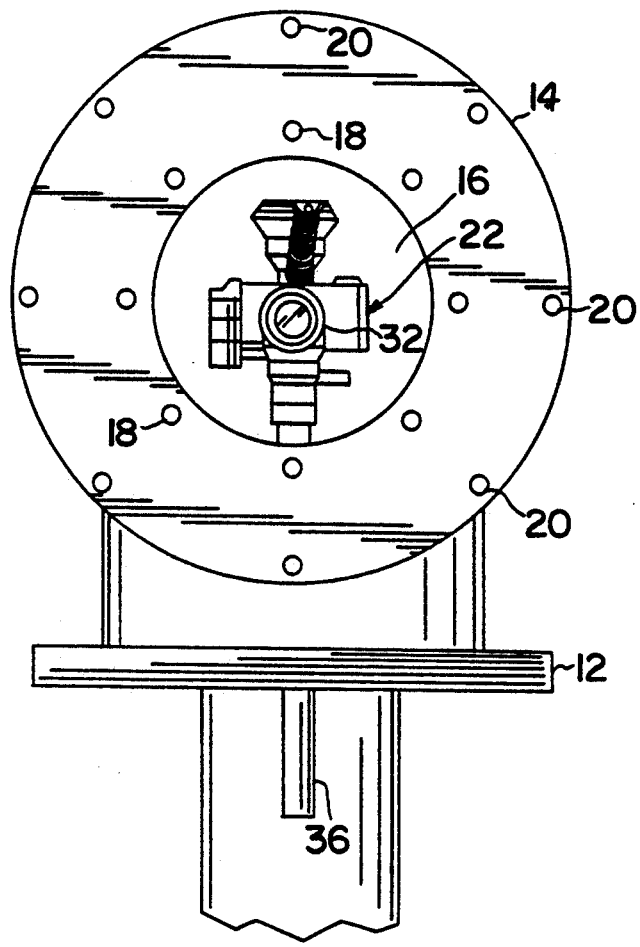
FIG. 2 is a front view of the photo-deviometer of FIG. 1.

Referring now to FIG. 2, the lens 30 of the camera is located in the central portion of the central fixation opening 16 of the disk 14. Referring now to FIG. 3, a Patient "P" has her head adjusted by the adjustable headrest 24 so that her eyes are directly in line with the central fixation opening 16 to the center of the lens 30 of the camera 22. Thus, the Patient "P" focuses on the film plane as opposed to some point in between.

Figure 7:
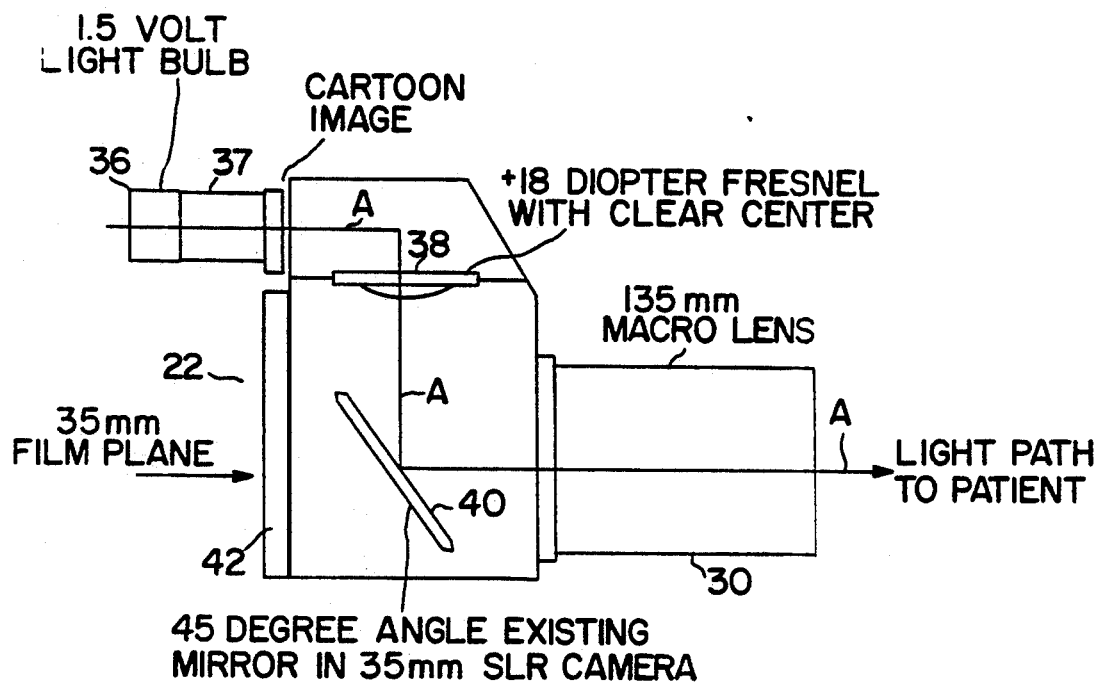
FIG. 7 is an enlarged diagrammatic side view of a 35 mm SLR camera illustrating the existing mirror at 45° and image projection systems.
Figure 8:
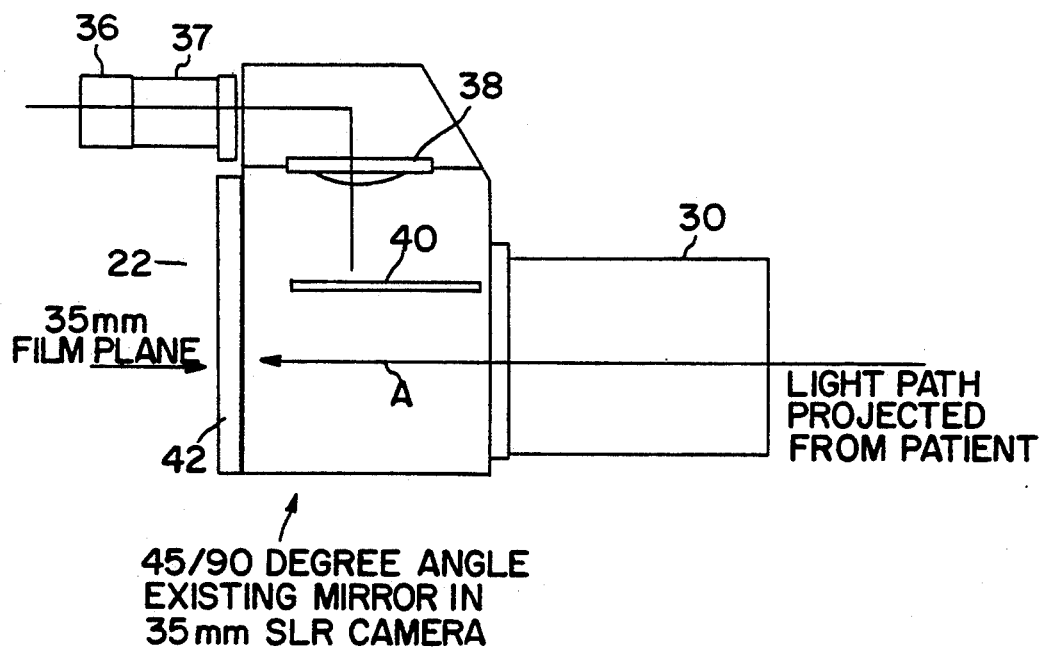
FIG. 8 is a view similar to FIG. 7 with the mirror at 90° while recording the patient's central fixation.
Figure 9:
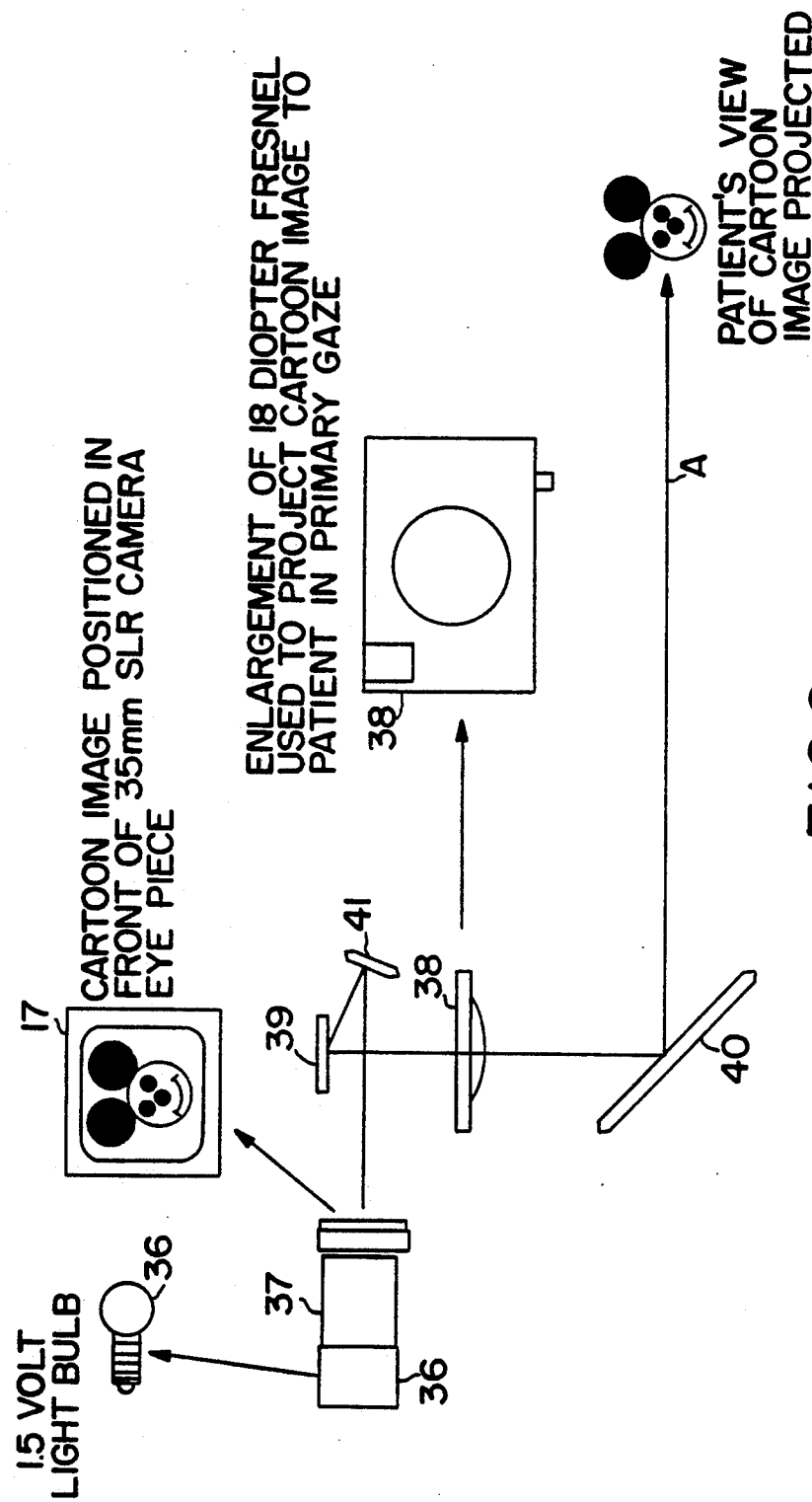
FIG. 9 is a schematic view of the primary gaze position projection system.

Referring now to FIGS. 7, 8, and 9, the camera 22 has attached to it a 90° view finder 36, a +18 diopter fresnel 38 with clear center, a 45° angle mirror 40, which is the existing mirror in a 35 mm SLR camera 22 and the lens 30, here shown as a 135 mm macrolens. The 35 mm film plane is indicated by the reference numeral 42 and the light path to the patient is indicated by the reference letter A.

The 90° view finder 36 is attached to the view finder of the 35 mm SLR camera 22 which illuminates an accommodative target 17, a cartoon character, which is viewed by the Patient "P." This method of single illumination accommodative target has been selected so as to attract the patient's attention to that specific image. This was done especially due to the fact that the operator must deal with young patients that often present with a low attention span. Thus, this system provides true central fixation. In the past, a single red diode mounted on the top of a flash was positioned under the front portion of a 35 mm macrolens to serve as a central fixation target, but this yielded inaccurate results firstly because it was a nonaccommodative target. Secondly, the subject ended looking at a fixation target that was too low and that was 22 cm away from the film plane. The current central fixation device was made partially possible by using the number 9 endoscopic photo Fresnel 38 (a focusing screen from the Olympus Corporation). The number 9 Fresnel has a clear surface with its center, which is 23 mm in diameter, acting as a +18 Diopter lens. This in turn magnifies the image that is projected from the 90° view finder 36 through the SLR camera 22 and the macrolens system 30. Thus, the Patient "P" focuses on the film plane as opposed to some point in between and a true accommodative fixation device is provided. The image is introduced simply by using the proper illumination switch. The image also can be taken out of view by rotating a lever (not shown) on the view finder or simply removing the 90° view finder from the SLR camera eyepiece.

Referring now to FIG. 7 and particularly to FIG. 9, as previously mentioned, the photo-deviometer is equipped with a central fixation device that is unique because it permits recording the patient's central fixation while the patient is fixating and accommodating on the film plane or film grain 42 of the 35 mm SLR camera, as illustrated in FIG. 8. This is achieved by utilizing a view finder 36 utilizing a 1.5 volt bulb in the projection system attached to the 35 mm eyepiece 37. A cartoon image 17 is placed in the projection system 36 and can be interchanged at any time for another cartoon image. The light is then reflected by the three existing mirrors 39, 41, and 40 inside the head of the 35 mm SLR camera through the 18 diopter lens 38 that magnifies the image projected through the SLR camera lens 30. The cartoon image 17 is then reflected by the existing 35 mm internal mirror 40 and finally projected through the 135 mm macrolens 30. During the time when the patient's eye is covered, the preferred eye can accommodate on a preselected image, the covered eye will relax and drift, demonstrating primary position of gaze. FIG. 7 illustrates the position of the mirror 40 when the patient can see projected central fixation image 37, and FIG. 8 illustrates the position of the mirror 40 position up and the patient momentarily cannot see the image during the time of photography in the primary position of fixation.

In the presence of a manifest strabismus, the Patient "P" sees the image with only one eye and, therefore, the fixating eye or the preferred eye should be used to record accurate results. This can be achieved by using the cover test system. As this image is being projected to the Patient "P," the operator can depress either a hand or foot switch and for one-sixtieth of a second, the mirror 40 of the 35 mm camera 22 pops up (the image can no longer be seen) and the photograph of true central fixation is achieved. At this point, the image 17 reappears to the patient until an alternate image is selected on the fixation wheel or disk 14. When the photograph is taken in this primary gaze, the light illuminating the image is turned off for a period of one-fiftieth of a second. This occurs so that the light traveling through the prism head and lens coming from the 90° view finder 36 will not affect the automatic exposure of the SLR camera 22.

The camera 22 must, however, stay stationary, that is at the same elevation as the 3 and 9 o'clock fixation positions to yield accurate and reproducible results. Since the distance from the Patient "P" to the lens 30 is fixed, it is not necessary to refocus between patients.

As an example of a photo-deviometer according to the invention by which the foregoing advantageous results are achieved, a photo-deviometer 10 was constructed which included an adjustable table 120 cm in length and 42 cm in width. The circular wheel 14 with the inner and outer rows of fixation targets 18 and 20 was 54 cm in diameter with a 26.5 cm fixation opening 16 in the center. This opening was made so that a 35 mm SLR camera equipped with a ring flash could be positioned centrally on a mono pod 36. The visual images on the wheel 14 were mounted on the back of a blackboard shaped to fit the wheel 14 which was positioned with strips of velcro onto the front part of the wheel. The image wheel could be interchanged for new images at any time. The images selected, as previously mentioned, were Walt Disney characters.

The recording device 22 was an Olympus OM-4 35 mm SLR camera with an autowinder sitting on the monopod 36 and controlled either by a hand switch or a foot switch. A foot switch is very useful when doing a cover test or when photographing a down gaze where both hands of the operator may be necessary to hold the eyelids of the patient open. Attached to the camera 22 was a 135 mm macrolens 30 with a bellow extended to 17 cm. The f stop was preset at F22 for good depth of field. If desired, the camera can be fitted with a datapak that would imprint on the film, preferably in the lower right hand corner, the patient's identification number, the date or the time of the day.

Figure 10:
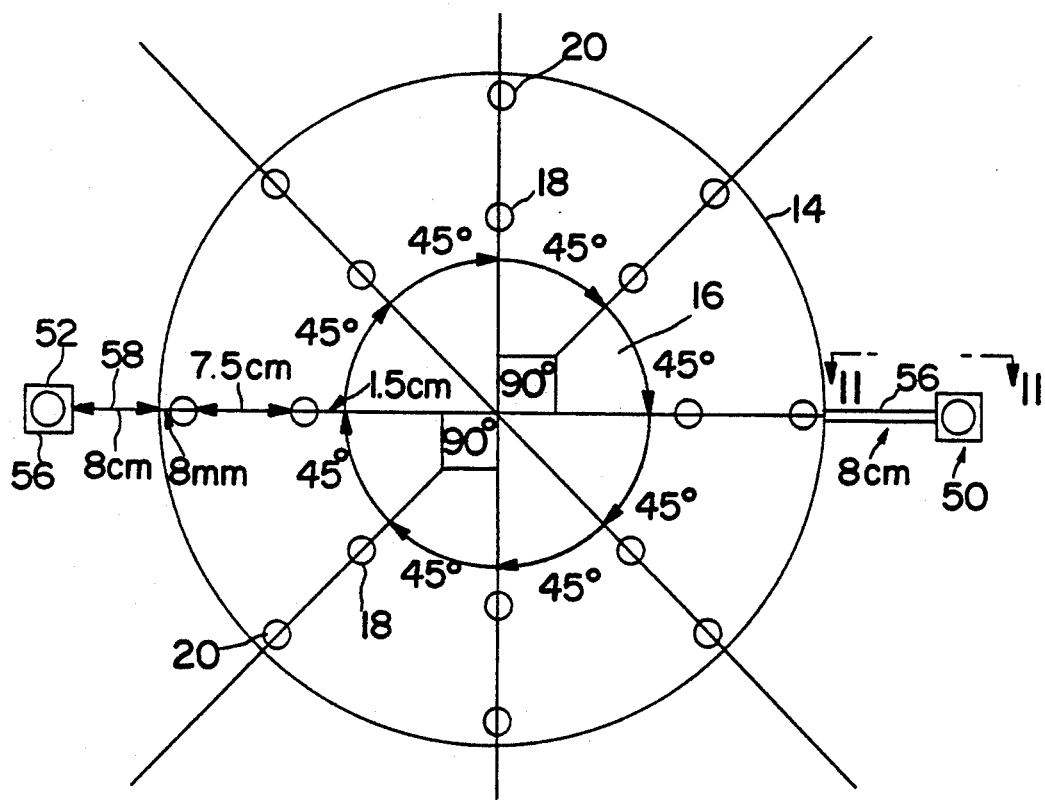
FIG. 10 is a front view of a deviometer disk provided with external fixation devices.
Figure 11:
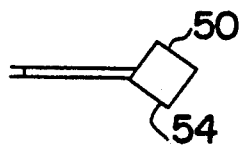
FIG. 11 is a cross-sectional view taken along the line 11—11 of FIG. 10.

Referring now to FIGS. 10 and 11, the photo-deviometer disk 14 may be provided with first and second external or outer fixation images 50 and 52, respectively, preferably located at opposite sides of the disk 14 at the 3:00 and 9:00 o'clock positions. For convenience, the images 50 and 52 may be plugged into the side of the disk 14 on arms 56 and 58, respectively, such as eight cm long. The fixation images 50 and 52 are preferably 4×4×4 cm cubes. The images 50 and 52 have a front wall 54 and 56 having an opening with a fixation target therein. The front walls 54 and 56 are preferably angled forward at 35° towards the patient to facilitate patient fixation. The purpose of the images 50 and 52 are to measure the maximum or exaggerated high movement of the eyes of the patient.

An Olympus T-10 ring flash 31 with recycling flash time of four seconds set on ASA 400 and the automatic position was used which was mounted directly on the macrolens 30 which was 52 mm in diameter. Kodak Ectachrome EL-400ASA film with a preset speed of 1/60th on the camera was used.

Highly satisfactory, accurate and reproducible measurements and photographs were obtained.

When performing deviometry measurements, the operator normally sits on the left side when doing the right gazes and on the right side when doing the left gazes. When the photographs are taken, the same principle applies. Care must be taken to ensure that the patient is using the fixating eye when fixating at the different accommodative targets. This can be easily accomplished with the cover technique. The pediatric subject can be measured in either the standing or sitting position, on the parent's lap and, if older, in an examining chair. If desired, for added accuracy, a special counting grid used in endothelial cell photography can be used. This grid has 2 mm squares. It is placed at the film plane of the camera and will help to measure any eye deviation.

Figure 12:
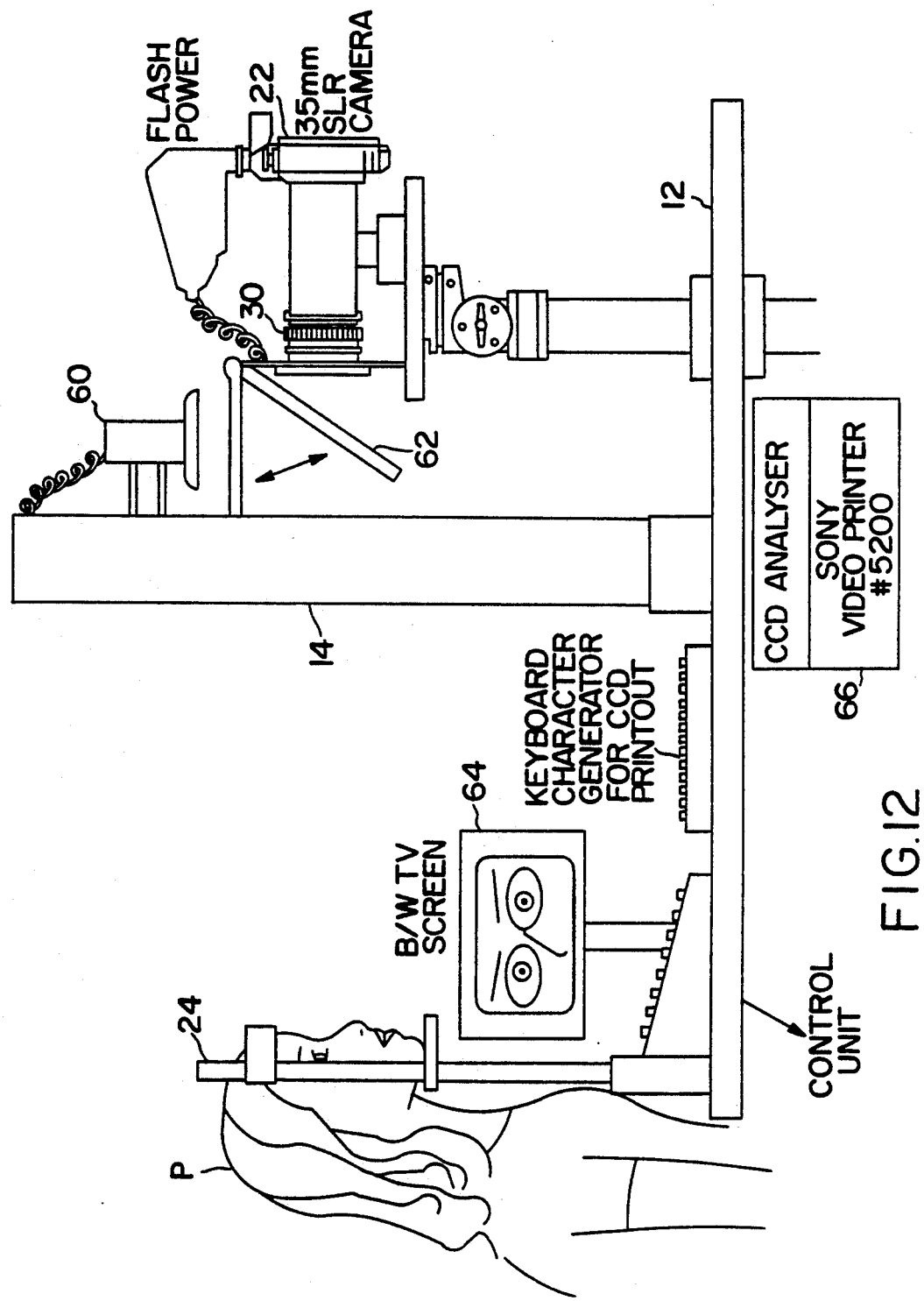
FIG. 12 is a side elevational view of a photo-deviometer with the addition of a video camera and monitor for viewing the patient's gaze.
Figure 13:
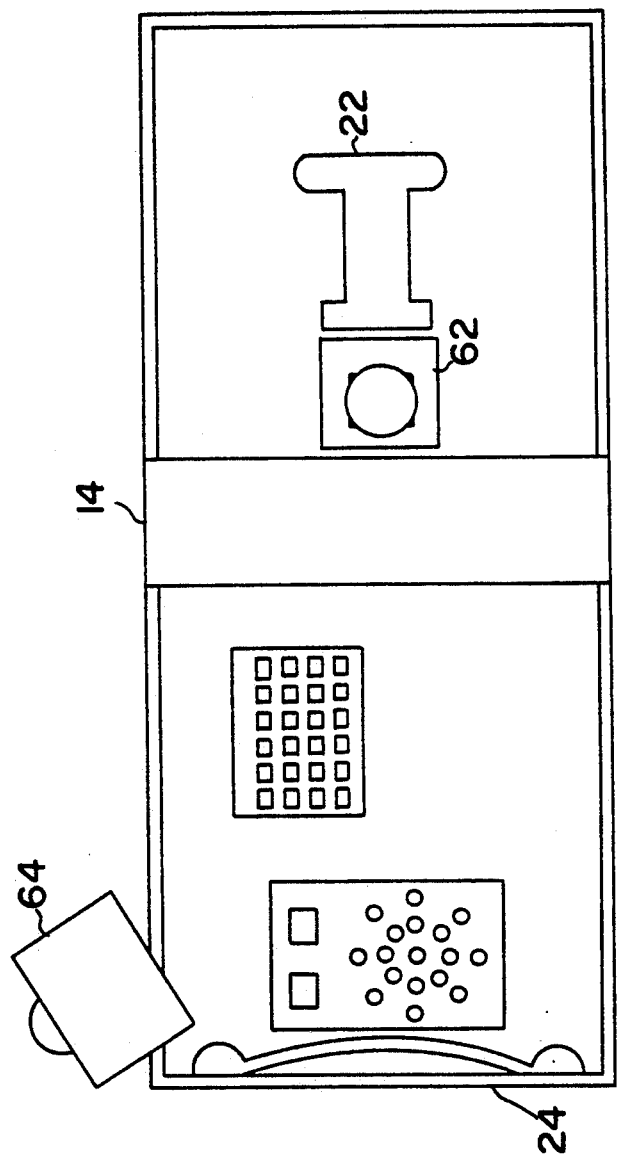
FIG. 13 is a top view of the photo-deviometer of FIG. 12.

However, the operator sitting at the left or right hand of the patient is not able to easily determine if the patient's fixating eye is properly directed. In order to overcome this problem, a video monitor and screen may be used to give the operator a direct view of the patient's eyes. Referring now to FIGS. 12 and 13, a conventional video monitor 60, such as a conventional T.V. camera or charged coupled device (C.C.D.) T.V. camera may be mounted to obtain a view of the patient's face. Thus, a mirror 62 is movable into and out of the central fixation position between the camera 22 and the headrest 24. When the mirror 62 is in the position, as best seen in FIGS. 12 and 13, the mirror 62 projects an inline view of the patient's face to the camera 60. The camera 60 is operatively connected to a video screen, such as a T.V. screen 64, which can be mounted for ease of viewing by the operator. The picture on the screen 64 thus provides the operator with a full front direct view of the patient's face and thus of the fixation position of the patient's eyes. A print of the fixation position of the patient can be obtained by the video printer 66. The mirror 62 is moved out of position from the front of the camera 22 while taking pictures.

The photo-deviometer according to the present invention allows both measurement and photographic documentation of the strabismus in the cardinal positions of gaze. The photo-deviometer may be operated by only one person, be it the ophthalmologist, ophthalmic photographer, or other allied help professional. The examiner can control the patient, the fixation target, and the SLR camera all at the same time. Since both measurements and photographs are obtained simultaneously, this instrument has proved to be a time saving device.

By using the ring flash, the operator will automatically produce a corneal specular reflection simulating the Hirshberg test. This can be very useful in evaluating one eye over the other.

Accordingly, the present invention attains the objects and ends and has the advantages and features mentioned as well as others inherent therein.

While presently preferred embodiments of the invention have been given for the purposes of disclosure, changes may be made therein which are within the spirit of the invention as defined by the scope and the appended claims.

What is claimed is:

1. A photo-deviometer comprising:
   a support structure,
   a camera mounted on the support structure,
   an adjustable headrest for fixing a patient's head mounted on the support structure and spaced from the camera,
   a deviometer disk mounted on the support structure between the camera and the head rest, the deviometer disk having a central fixation opening,
   the camera, headrest and deviometer disk arranged so that the patient's eyes when the headrest is in an adjusted position is in a central fixation position through the central fixation opening and in the camera's film plane,
   a plurality of fixation image targets on the deviometer disk facing the patient provided with a manually activated switch for each of the fixation image targets operable to illuminate individually each of the fixation image targets, the camera provided with a viewfinder having a central illuminated fixation image and having a mirror arranged so that the patient sees the central illuminated fixation image in the mirror while in the central fixation position, whereby, the patient while in the central fixation position can look at, fixate on and accommodate to the central illuminated fixation image and a photograph can be taken of the patient's eyes while so doing, a second mirror movable into and out of the central fixation position between the camera and the headrest, a video monitor positioned to view the mirror when the second mirror is positioned in the central fixation position for viewing a patient's eyes, and a video screen mounted on the support structure for viewing by a photo-deviometer operator.

2. The photo-deviometer of claim 1 where the second mirror is pivotally movable between the disk and the camera into a 45° angle relative to the central fixation opening, and the video monitor is positioned behind the disk and above the central fixation opening.

* * * * *